USOO9005212B2

(12) United States Patent
Berberich et al.

(10) Patent No.: US 9,005,212 B2
(45) Date of Patent: Apr. 14, 2015

(54) DEVICE FOR GUIDING A DRILLING TOOL FOR FORMING A SECOND BORE IN A BONE (75) Inventors: Sascha Berberich, Tuttlingen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1284 days.

(21) Appl. No.: 11/962,581

(22) Filed: Dec. 21, 2007

(65) Prior Publication Data
US 2008/0154271 A1    Jun. 26, 2008

(30) Foreign Application Priority Data

Dec. 22, 2006 (DE) .......................... 10 2006 062 382

(51) Int. Cl.
*A61B 17/56* (2006.01)
*A61B 17/17* (2006.01)

(52) U.S. Cl.
CPC ......... *A61B 17/1714* (2013.01); *A61B 17/1764* (2013.01)

(58) Field of Classification Search
USPC ................... 606/87, 88, 96, 98, 99
See application file for complete search history.

(56) References Cited

U.S. PATENT DOCUMENTS

| 4,722,331 | A | | 2/1988 | Fox |
| 5,688,284 | A | * | 11/1997 | Chervitz et al. ................ 606/96 |
| 5,893,878 | A | * | 4/1999 | Pierce ........................... 606/207 |
| 6,254,605 | B1 | | 7/2001 | Howell |
| 6,595,999 | B2 | * | 7/2003 | Marchione et al. ............ 606/96 |
| 6,994,725 | B1 | | 2/2006 | Goble |
| 2004/0087953 | A1 | | 5/2004 | Singhatat et al. |
| 2006/0069394 | A1 | | 3/2006 | Weiler et al. |
| 2007/0123902 | A1 | | 5/2007 | Berberich et al. |
| 2007/0191852 | A1 | | 8/2007 | Shimko et al. |

FOREIGN PATENT DOCUMENTS

| DE | 3312250 A1 | 10/1984 |
| EP | 1642538 A2 | 4/2006 |
| EP | 1714619 A1 | 10/2006 |

* cited by examiner

*Primary Examiner* — Christian Sevilla
(74) *Attorney, Agent, or Firm* — St. Onge Steward Johnston & Reens LLC (57) ABSTRACT A device serves for guiding a drilling tool for forming a second bore in a bone, which second bore intersects an already existing first bore. A frame, having a first end and a second end has a rod-shaped body arranged at its first end. Said rod-shaped body is designed to be inserted into said already existing first bore. A guide sleeve is arranged at said second end of said frame and has a longitudinal axis intersecting said rod-shaped body in an area of its distal end. A fixing device is provided at said guide sleeve, said fixing device protrudes distally from said guide sleeve, said protruding fixing device can be placed on a body of a patient to be treated in an area where said second bore is to be formed.

8 Claims, 6 Drawing Sheets

DEVICE FOR GUIDING A DRILLING TOOL FOR FORMING A SECOND BORE IN A BONE

BACKGROUND OF THE INVENTION

The invention relates to a device for guiding a drilling tool for forming a second bore in a bone, which second bore intersects an already existing first bore.

A device for guiding a drilling tool and having these design features is known from U.S. Pat. No. 6,540,783 B1.

Such a device is used for fixing a tendon replacement fitted in a bone, mostly in the area of the knee joint.

For this purpose, a drilling tool is used to form a first bore in the bone, said bore extending both through the thigh bone (femur) and also through the shin bone (tibia). A tendon replacement is pushed into this first bore.

To fix this tendon replacement, a transverse pin is introduced which is driven transversely into the tendon replacement or into a loop in the tendon replacement, such that the tendon replacement is fixed by this transverse pin against being pulled out of the first bore.

To introduce the transverse pin, it is necessary to produce an additional second bore in the thigh bone, said second bore being oriented such that it intersects the first bore, that is to say extends transversely, mostly at right angles, with respect to the latter.

Since, from this transverse direction, the position of the first bore in the bone is not visible to the operator, auxiliary devices or sighting devices have been created with which this second bore extending transversely with respect to the first bore can be arranged precisely in the correct position for introduction of the transverse pin, i.e. in such a way that this second bore meets the first bore.

The aforementioned device known from U.S. Pat. No. 6,540,783 B1 has an L-shaped frame at whose first end a rod-shaped sleeve is arranged through which a guide wire can be guided, which can be inserted into the already existing bore in the femur and the tibia. At the second end of the L-shaped frame there is a guide element comprising two through-openings.

When producing a second bore in the bone that extends transversely with respect to the first bore, the guide wire received in the sleeve is first introduced into the first bore in the tibia and the femur. A guide sleeve that serves to receive a trocar or a drilling tool is pushed into each of the openings in the guide element. After a trocar has been inserted into the two guide sleeves in each case, the guide sleeves, with the trocars received in the sleeves, are driven into the femur, specifically such that the tips of the trocars do not yet extend into the first bore in the bone.

Thereafter, both the L-shaped frame and also the sleeve arranged at the first end of the frame are pulled off with the guide wire, and the tendon replacement is pushed into the first bore. The two trocars with the guide sleeves are then driven further into the femur, such that the tendon replacement located in the first bore is pierced by them. The trocars are then removed, and two transverse pins are introduced through the guide sleeves remaining in the second bores in order to secure the tendon replacement against being pulled out of the first bore in the bone.

In order to introduce the transverse pins precisely into the respective second bore in the bone using this device, it is necessary that the two guide sleeves are inserted into the bone of the patient and initially remain in the bone, especially after the L-shaped frame and the sleeve have been drawn off with the guide wire.

After the transverse pins have been introduced into the second bore, the guide sleeves still present in the second bore have to be removed from the bone.

However, this proves to be a disadvantage, because removing the guide sleeves can cause a change of position of the transverse pins introduced into the second bore.

In the bone, the guide sleeves cause a channel which is quite a bit larger than is necessary for insertion of the transverse pin. Moreover, since two such channels are produced, there is an unnecessarily high degree of excavation and, consequently, a weakening of the bone in this area. If revision surgery had to be performed later, relatively large areas of the bone would already be weakened by the two channels.

It is therefore an object of the present invention to develop a device of the type mentioned at the outset in such a way that the transverse pin can be introduced and precisely positioned without causing unnecessary trauma to the bone substance.

SUMMARY OF THE INVENTION

According to the invention this object is achieved by a device for guiding a drilling tool for forming a second bore in a bone, which second bore intersects an already existing first bore, comprising a frame, having a first end and a second end, a rod-shaped body arranged at said first end of said body, said rod-shaped body is designed to be inserted into said already existing first bore in said bone, a guide sleeve for guiding said drilling tool is arranged at said second end of said frame, a longitudinal axis of said guide sleeve intersects said rod-shaped body in an area of a distal end of said rod-shaped body, wherein a fixing device is provided at said guide-sleeve, said fixing device protrudes distally from said guide sleeve, said protruding fixing device can be placed on a body of a patient to be treated in a area said second bore is to be formed.

This measure has the considerable advantage that, when the fixing device protruding distally from the guide sleeve is placed on the body of the patient in the area where the second bore is to be formed, the guide sleeve is fixed in a position which is chosen by the operator and which is suitable for formation of the second bore, without the guide sleeve having to be driven into the bone.

When forming the second bore in the bone using the device configured in this way, the rod-shaped body is first inserted into the first already existing bore in the bone, and the guide sleeve is fixed by placing the fixing device on the patient's body in the area where the bore is to be arranged. The contact pressure of the fixing device is generated via the frame and the rod-shaped body that is engaged in the first bore. A drilling tool received in the guide sleeve is used to produce the second bore, which transversely intersects the first bore. The diameter corresponds to the external diameter of the transverse pin, that is to say the bore channel is exactly the size required and no larger.

Thereafter, the frame and the rod-shaped body are withdrawn, and the drilling tool received in the guide sleeve is drawn back until the first bore lies free. The tendon replacement is then pushed into the first bore and, after removal of the drilling tool, and by way of the guide sleeve still fixed in the desired position by means of the fixing device and located outside the bone, the transverse pin is inserted into the second bore and driven into a loop in the tendon replacement.

The fact that the guide sleeve does not have to be driven into the bone means that, after the transverse pin fixes the tendon replacement against pulling out of the first bore, said sleeve can be removed from the patient's body without any danger of the position of the transverse pin located in the inside of the bone being changed.

In other embodiments of the invention, the fixing device can be placed on the body of the patient over at least three fixing sites.

Placing the fixing device on the patient's body over at least three fixing sites ensures that the fit of the guide sleeve on the patient's body during the intervention is stable and, in particular, secure against tilting.

By providing three fixing elements, the guide sleeve has a firm hold during production of the second bore and during introduction of the transverse pin into the second bore, such that the guide sleeve is secured against undesired movements.

In another embodiment of the invention, the fixing elements are arranged on a holder body.

This measure has the advantage that the fixing elements are supported by a holder body via which the contact pressure can be exerted.

In another embodiment of the invention, the fixing elements are distributed uniformly about the circumference of the holder body.

This measure has the advantage that, by distributing the at least three guide elements uniformly about the circumference of the holder body, the guide sleeve is fixed securely and evenly on the patient's body in the area where the bore is to be formed, as a result of which the stability of the fixing of the guide sleeve during the surgical intervention is secured.

In another embodiment of the invention, the fixing elements are designed as radially protruding legs.

This measure has the advantage that, for one timing, the design of the guide elements as radially protruding legs permits a structurally very simple way of designing the fixing device for the aforementioned functions. The radially protruding legs arranged on the holder body form three fixing points which the operator can see clearly at all times both during their placement and during the surgical intervention. Thus, if necessary, the operator is able to correct the fixing at the fixing points, which further increases the stability of the fixing of the guide sleeve during the surgical intervention.

In another embodiment of the invention, ends of the fixing elements are hook-shaped.

This measure has the advantage that the hook-shaped ends of the fixing elements dig into the skin and ensure a stable hold of the guide sleeve during the surgical intervention.

In another embodiment of the invention, the holder body is flexible.

This measure has the advantage that the fixing device adapts to uneven surfaces of the body. This is the case in operations in the area of the knee.

When placed on an uneven surface of the body, the fixing elements arranged on the holder body exert a certain force on the holder body. The force exerted on the holder body made of flexible material causes its deformation, such that the fixing elements can adapt to the uneven surface of the patient's body in the area where the bore is to be formed.

In another embodiment of the invention that can be used as an alternative to the aforementioned embodiment, the fixing elements are adjustable.

In this embodiment of the invention too, it is possible, by structurally simple means, to ensure that a device of this kind can be securely fixed on uneven body surfaces.

In another embodiment of the invention, the holder body is designed as a ring-shaped element.

This measure has the advantage that a ring-shaped element represents a very stable and easy-to-produce configuration of the holder body.

By arranging the opening in the holder body such that it is in the axial continuation of the channel extending through the guide sleeve, it is possible for a drilling wire or drilling tool to be passed through the channel in the guide sleeve and through the opening in the holder body.

In another embodiment of the invention, the holder body is connected to the guide sleeve via a ball joint.

This measure has the advantage that a ball joint is an articulated connection of two structural elements which is technically easy to produce, yet secure, and through which it is possible directly to achieve the desired angle settings of the holder body, and thus of the fixing elements arranged thereon, relative to the longitudinal direction of the guide sleeve.

It will be appreciated that the aforementioned features and those still to be explained below can be used not only in the cited combinations, but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which.

DETAILED DESCRIPTION OF PREFERRED EMBODIMENTS

In FIGS. 1 to 6, a device for guiding a drilling tool for forming a second bore in a bone is designated in its entirety by reference number 10.

Figure 1:
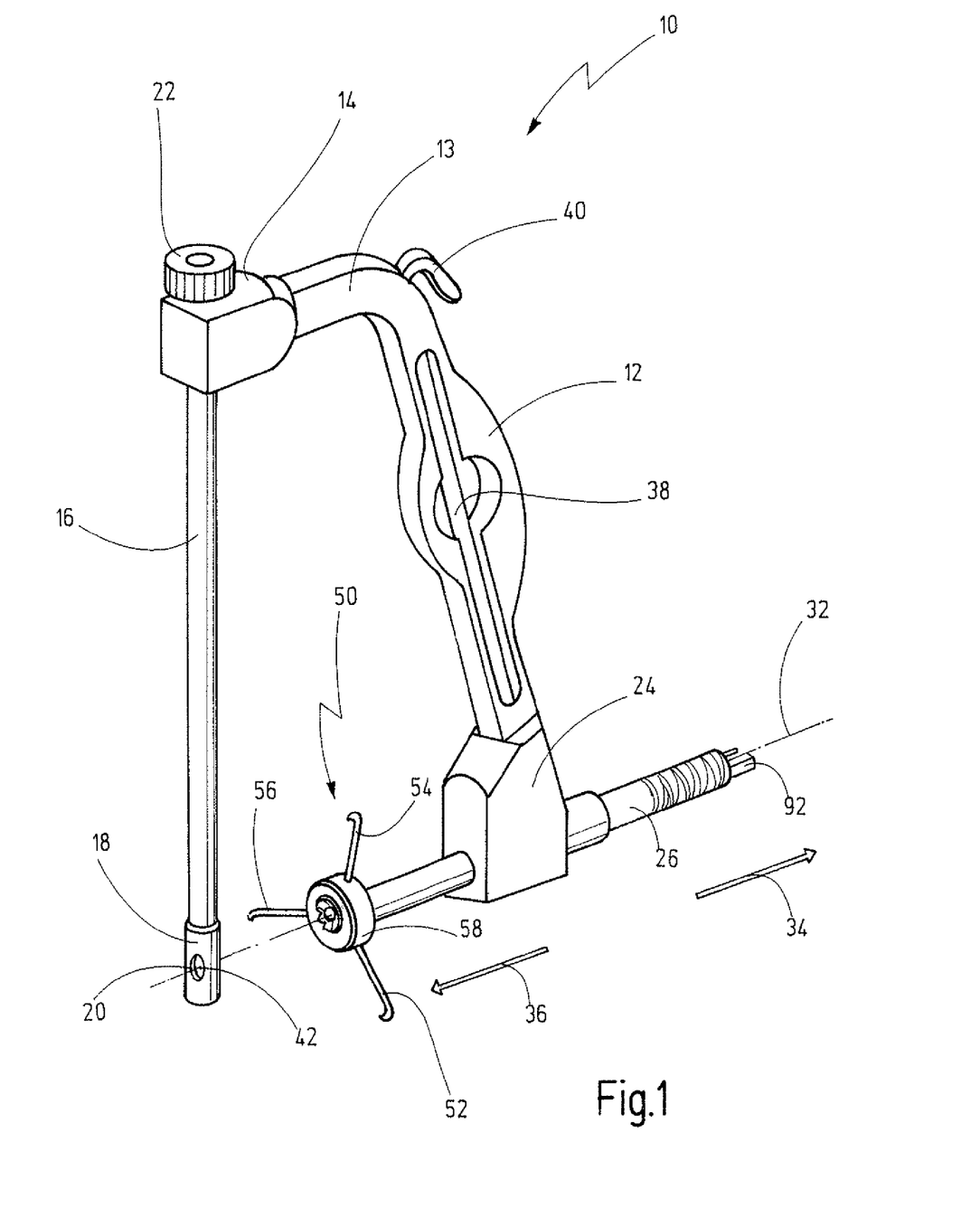
FIG. 1 shows a perspective side view of a device according to the invention.

The device 10 has a frame 12 which, in this illustrative embodiment, is designed as an L-shaped bracket 13.

Figure 5:
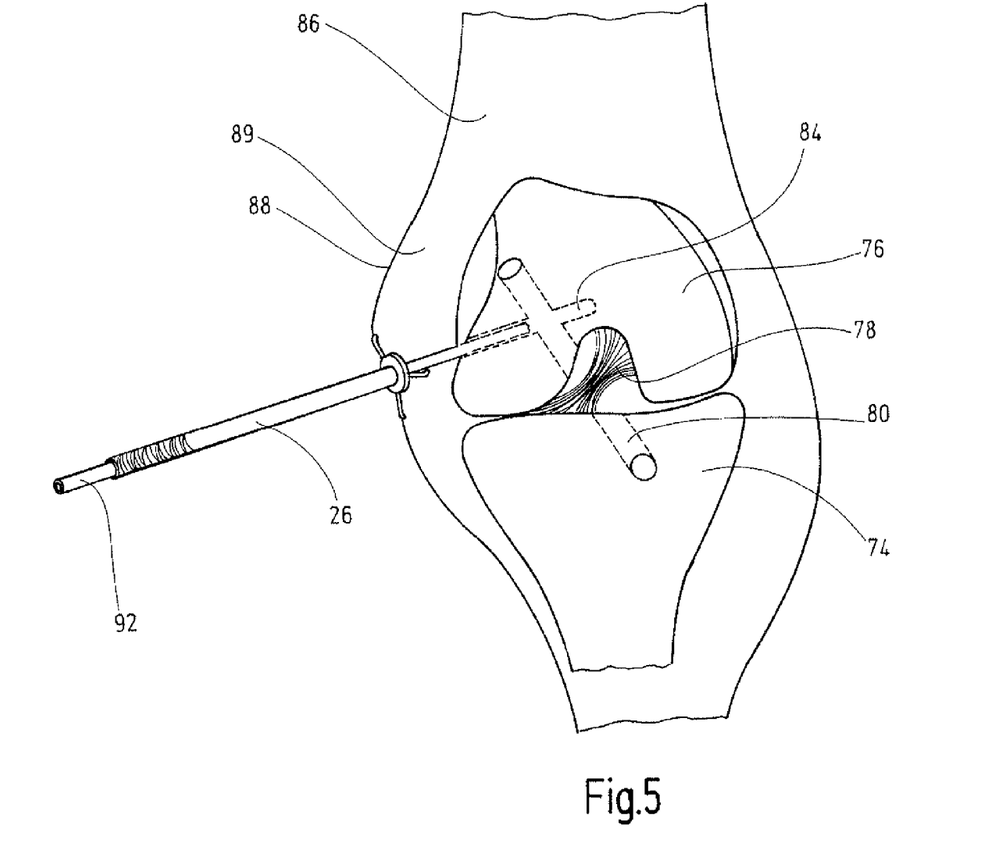
FIG. 5 shows a view comparable to that of FIG. 4, with the frame and the rod-shaped body having been withdrawn.
Figure 6:
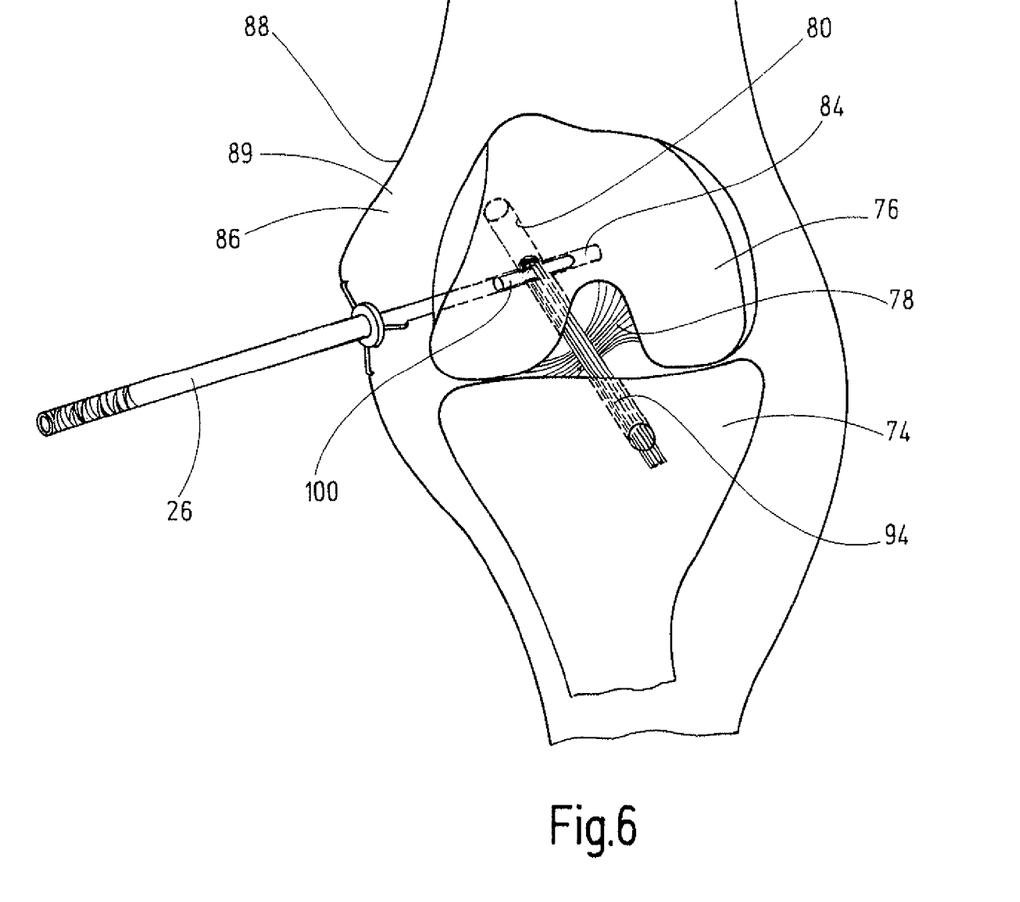
FIG. 6 shows a view comparable to that of FIG. 5, with a tendon replacement having been pushed into the first bore in the bone and a transverse pin having been inserted into the second bore.

Arranged at a first end 14 of the frame 12 there is a rod-shaped body 16 which can be inserted into an already existing first bore in a bone, as will be described in more detail below with reference to FIGS. 4 to 6.

The rod-shaped body 16 has a circular cross section.

An opening 20 in the form of a continuous transverse bore is present at a distal end 18 of the rod-shaped body 16. The rod-shaped body 16 is hollow.

The rod-shaped body 16 is connected releasably to the first end 14 of the frame 12 by a screw 22.

A guide sleeve 26 is received displaceably in a second end 24 of the frame 12. A channel 28 extends through the guide sleeve 26, as is shown in particular in the sectional view in FIG. 2. A drilling tool 92 can be received in the channel 28, as can be seen from FIG. 1.

Figure 2:
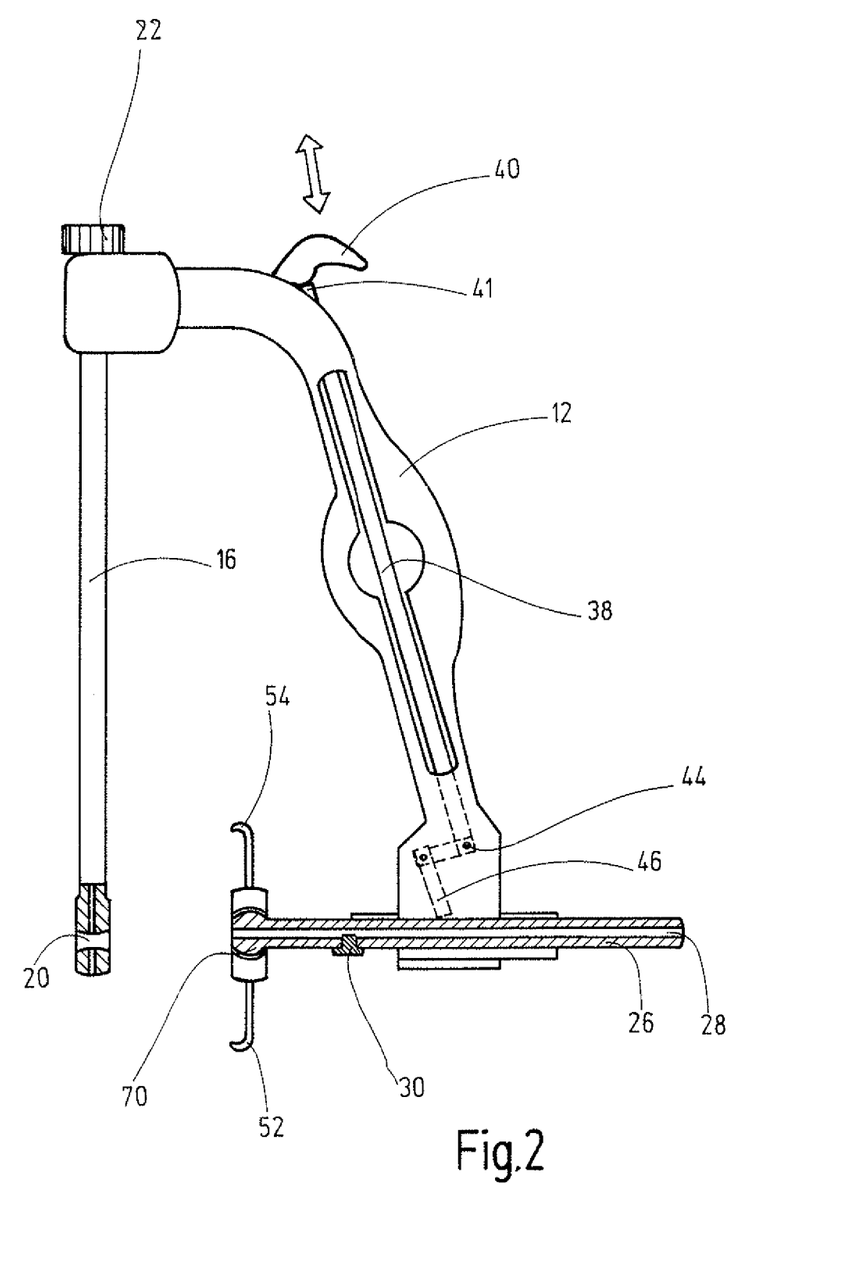
FIG. 2 shows the device from FIG. 1 in a partially sectioned side view, with no drilling tool received in the guide sleeve.
Figure 3:
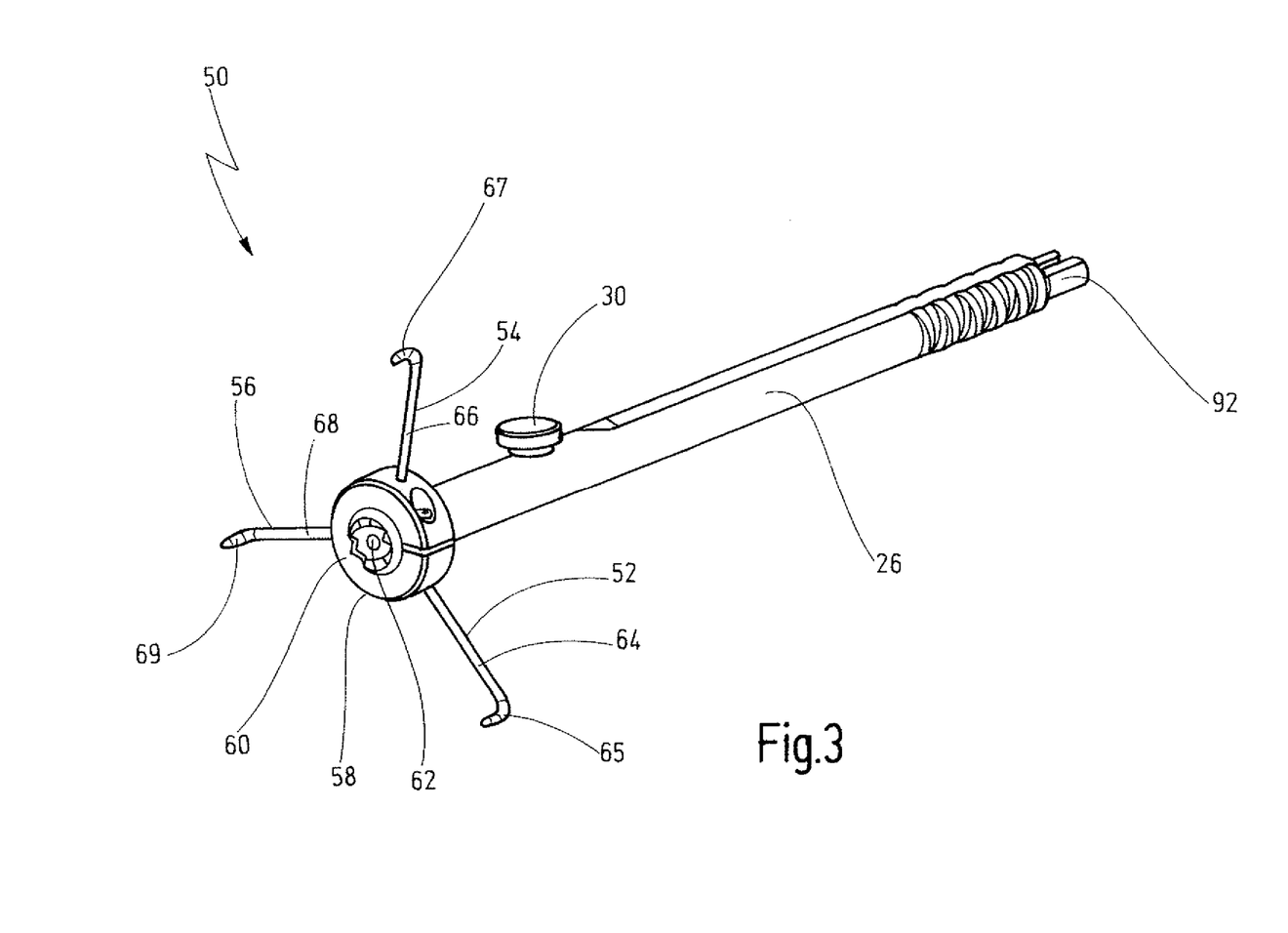
FIG. 3 shows an enlarged view of the guide sleeve and of the fixing device protruding distally from the guide sleeve as in FIG. 1.

It will be seen from the views in FIGS. 2 and 3 that the guide sleeve 26 has a locking screw 30. The locking screw 30 is used to fix a drilling wire or drilling tool 92 which is received in the channel 28 of the guide sleeve 26 and which can be displaced to and fro.

The guide sleeve 26 itself is also displaceable to and fro along its longitudinal axis 32 in the second end 24, as is indicated by arrows 34, 36 in FIG. 1.

A clamping device is used to lock the guide sleeve 26 by clamping.

A movable clamping bar 38 is arranged in the L-shaped bracket 13 of the frame 12. It can be actuated by a lever 40, which is arranged on an outer face of the frame 12 and is thus easy for an operator to actuate. A cam 41 of the lever 40 rests on the upper end of the clamping bar 38.

The lower end of the clamping bar 38 is connected to a pivot lever 44, of which one limb 46 can be brought into clamping connection with the outer face of the guide sleeve 26.

Pressing the lever 40 causes the limb 46 to bear on the guide sleeve 26, as a result of which the displacement of the guide sleeve 26 in the direction indicated by the arrow 34 is blocked.

Lifting the lever 40 releases the pivot lever 44 and thus the guide sleeve 26.

It will be seen from the views in FIGS. 1 and 2 that the guide sleeve 26 is oriented in such a way that its longitudinal axis 32 is oriented towards a location 42 lying approximately at the centre of the opening 20 in the rod-shaped body 16. Said opening 20 is arranged at a distal end area 18 of the rod-shaped body 16.

When, as will be described in more detail below, a guide wire or drilling tool is pushed into the guide sleeve 26, it will be precisely directed along the longitudinal axis 32 to the opening 20 at the distal end 18 of the rod-shaped body 16.

A distally protruding fixing device 50 is arranged on the guide sleeve 26.

In the illustrative embodiment shown, the fixing device 50 is arranged on a distal end of the guide sleeve 26.

The fixing device 50 has a holder body 58 on which three guide elements 52, 54, 56 are arranged. In this illustrative embodiment, the holder body 58 is designed as an annular ring-shaped element 60. At the centre of the element 60 there is an opening 62, which is used to secure the holder body 58 on the distal end of the guide sleeve.

The fixing elements 52, 54, 56 are designed as radially protruding legs 64, 66, 68. Ends 65, 67, 69 of the fixing elements 52, 54, 56 are hook-shaped.

The fixing elements 52, 54, 56 designed as legs 64, 66, 68 are distributed uniformly about the circumference of the holder body 58, i.e. the fixing elements 52, 54, 56 are each mutually offset by approximately 120° on the holder body 58.

The holder body 58 is connected to the guide sleeve 26 via a ball joint 70, as can be seen from the sectional view in FIG. 2. Different angle settings of the holder body relative to the longitudinal direction of the guide sleeve 26 can thus be achieved. The spider-like legs 64, 66, 68, by virtue of their elasticity, permit more precise adjustment to uneven surfaces of the body.

The manipulation of the device 10 according to the invention will be explained briefly with reference to FIGS. 4 to 6.

Figure 4:
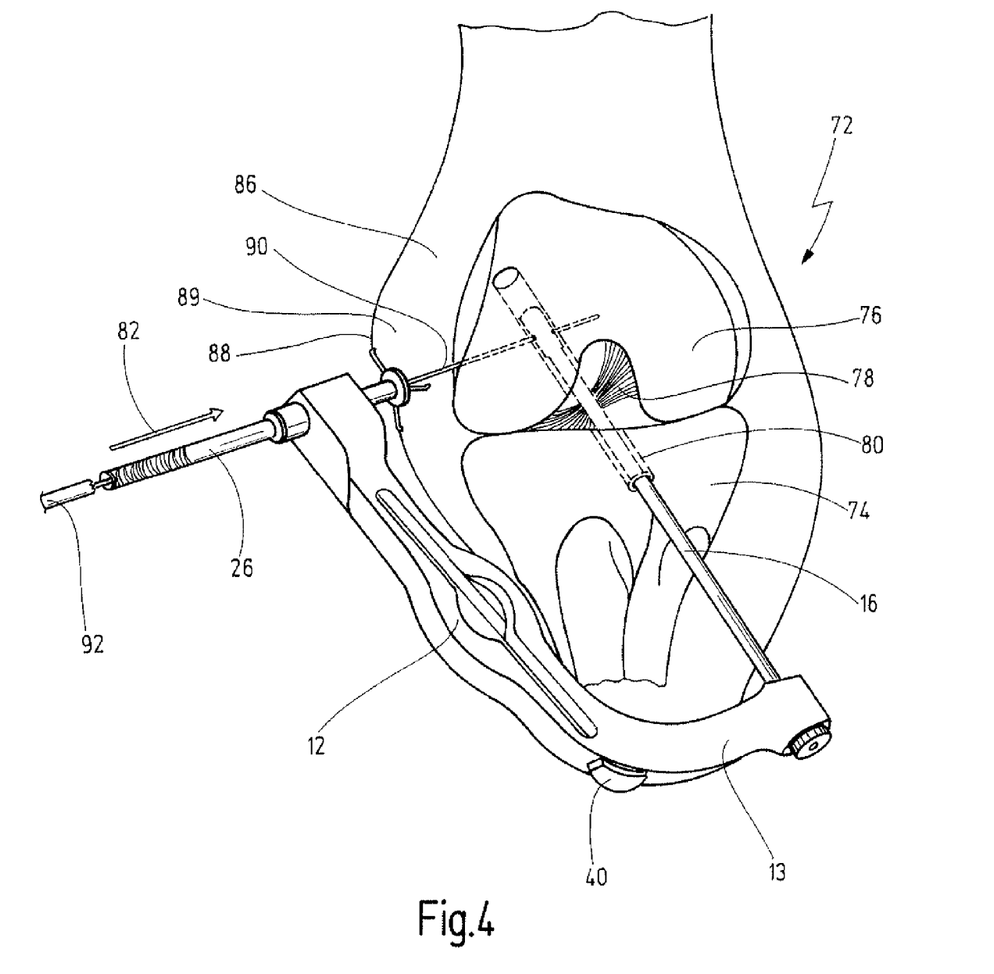
FIG. 4 shows a situation during the formation of a second bore in the reconstruction of an anterior cruciate ligament, with the whole device according to the invention from FIG. 1 being able to be seen.

FIG. 4 is a highly schematic representation of a human knee joint 72.

The knee joint 72 is a connecting joint between the tibia (shin bone) 74 and the femur (thigh bone) 76. Lying at the centre of the human knee there are two intersecting ligaments extending from the tibia 74 to the femur 76, namely the posterior cruciate ligament 78 and the anterior cruciate ligament, which is not shown here, and which is to be replaced by an implant.

In a reconstruction of the torn anterior cruciate ligament, as shown in FIG. 4, a surgical instrument is used first to produce a first bore 80 which extends both through the tibia 74 and also into the femur 76. The orientation corresponds approximately to the natural extent of the anterior cruciate ligament that is to be replaced. The bore 80 in most cases continues as far as the outer face of the femur 76 by way of a channel of small diameter.

The rod-shaped body 16 of the device 10 is inserted into the first bore 80. The guide sleeve 26 arranged at the second end 24 of the frame 12 is then targeted by the operator at an anatomically favourable site, with the fixing device 50 protruding distally from the guide sleeve 26.

The guide sleeve 26 with the fixing device 50 is then displaced by the operator in the direction indicated by an arrow 82 until the hook-shaped ends 65, 67, 69 of the fixing elements 52, 54, 56 reach the body 86 of the patient in the area where the second bore 84 is to be formed.

By further displacement of the guide sleeve 26, the hook-shaped ends 65, 67, 69 of the legs 64, 66, 68 dig through the skin 88 into the tissue 89, as a result of which the guide sleeve 26 is fixed in the position chosen by the operator for formation of the second bore 84.

By virtue of the ball joint 70, the fixing device 50 is able to adapt to irregularities of the patient's body, which is uneven in the area of the knee joint. In doing so, the orientation of the guide sleeve 26 does not change again. By locking the clamping device, the guide sleeve 26 remains in this position of longitudinal displacement. The rod-shaped body 16, engaged in the first bore, and the L-shaped bracket 13 exert the necessary contact pressure by means of the L-shaped bracket 13 being spread slightly away from the rod-shaped body. The second bore 84 can thus be formed with great precision.

Provision is also made to further improve the adaptation to irregularities of the patient's body 86 either by producing the holder body 58 from a resilient material or alternatively by making the legs 64, 66, 68 adjustable.

After the guide sleeve 26 has been fixed in the desired position on the patient's body 86 by means of the fixing device 50, a drilling wire 90 is first driven through the channel 28 of the guide sleeve 26 and through the skin 88 and tissue 89 into the femur 76, specifically until the drilling wire 90 passes through the opening 20 in the rod-shaped body 16 located in the first bore 80, as is shown in FIG. 4.

A hollow drill 92 is then driven through the channel 28, over the drilling wire 90, into the femur 76 and lies exactly in line with the opening 20 in the rod-shaped body 16.

After the second bore 84 has been formed, the clamped connection between L-shaped bracket 13 and guide sleeve 26 is released and the rod-shaped body 16 and the frame 12 are withdrawn. The guide sleeve 26 thus remains in the hollow drill 92 on or in the body. By virtue of the fixing device 50, the guide sleeve 26 remains on the body, protruding therefrom. The hollow drill 92 is drawn back until the first bore 80 lies free.

A prepared tendon serving as cruciate ligament replacement 94 is drawn in as a double loop into the first bore 80 with the aid of a pulling thread. The pulling thread 96 is then fixed on the outside of the body 86 using a fixing button 98.

The drilling tool 92 is now removed from the guide sleeve 26, and a transverse pin 100 is inserted through the channel 28 in the guide sleeve 26 and into the second bore 84. By means of the transverse pin 100, the cruciate ligament replacement 94 is fixed against being pulled out of the first bore 80.

The ends of the cruciate ligament replacement 94 are fixed in the first bore 80, e.g. by a bone dowel or further fixing button (not shown here).

What is claimed is:

1. A device for guiding a drilling tool for forming a second bore in a bone, which second bore intersects an already existing first bore, comprising
   a frame having a first end and a second end,
   a rod-shaped body arranged at said first end of said frame, wherein said rod-shaped body is designed to be inserted into said already existing first bore in said bone,
   a guide sleeve for guiding said drilling tool being arranged at said second end of said frame, a longitudinal axis of said guide sleeve intersecting said rod-shaped body in an area of a distal end of said rod-shaped body, and
   a fixing device provided at said guide sleeve, said fixing device protrudes distally from said guide sleeve, wherein said fixing device is capable of being placed on a body of a patient to be treated in an area where said second bore is to be formed, wherein said fixing device has at least three fixing elements comprising radially protruding legs having ends extended axially, which axially extending ends of said radially protruding legs are capable of digging through skin into tissue of the patient.

2. The device of claim 1, wherein said fixing elements are arranged on a holder body.

3. The device of claim 2, wherein said fixing elements are distributed uniformly about a circumference of said holder body.

4. The device of claim 1, wherein ends of said fixing elements are hook-shaped.

5. The device of claim 2, wherein said holder body is flexible.

6. The device of claim 1, wherein said fixing elements are adjustable.

7. The device of claim 2, wherein said holder body is designed as a ring-shaped element.

8. The device of claim 7, wherein said ring-shaped holder body is connected to said guide sleeve via a ball joint.

* * * * *